United States Patent
Gass et al.

(10) Patent No.: US 6,756,908 B2
(45) Date of Patent: Jun. 29, 2004

(54) CRACK DETECTION IN FRACTURE-CRITICAL MACHINE PARTS

(75) Inventors: Frank D. Gass, Hebron, CT (US); Gonzalo J. Rey, Glastonbury, CT (US)

(73) Assignee: United Technologies Corporation, Hartford, CT (US)

(*) Notice: Subject to any disclaimer, the term of this patent is extended or adjusted under 35 U.S.C. 154(b) by 0 days.

(21) Appl. No.: 10/036,267

(22) Filed: Dec. 28, 2001

(65) Prior Publication Data

US 2003/0122682 A1 Jul. 3, 2003

(51) Int. Cl.$^7$ .............................................. G08B 21/00
(52) U.S. Cl. ...................... 340/679; 340/680; 340/683; 73/600
(58) Field of Search ............................ 340/679, 680, 340/682, 683, 568.1; 73/600, 768, 774, 775, 128, 129; 324/557

(56) References Cited

U.S. PATENT DOCUMENTS

| | | | | |
|---|---|---|---|---|
| 3,985,318 A | * | 10/1976 | Dominey et al. | 244/17.11 |
| 4,026,660 A | * | 5/1977 | Ueda et al. | 416/61 |
| 4,106,332 A | * | 8/1978 | McKeown | 73/104 |
| 4,546,652 A | * | 10/1985 | Virkar et al. | 73/776 |
| 4,714,917 A | * | 12/1987 | Counter et al. | 340/679 |
| 5,952,836 A | * | 9/1999 | Haake | 324/718 |
| 5,969,260 A | * | 10/1999 | Belk et al. | 73/773 |

OTHER PUBLICATIONS

Barranger, J.P., "Eddy Current Jet Engine Disk–Crack Monitor", *Materials Evaluation*, Oct. 1984, pp. 1374–1378, vol. 42.

* cited by examiner

*Primary Examiner*—Benjamin C. Lee
*Assistant Examiner*—Phung T Nguyen

(57) ABSTRACT

A plurality of wires (33, 34; 35, 36) are disposed near the bottom (23–25) of blade root sockets (16–18) of a rotating disk 39 of a gas turbine engine by vapor deposition and etching, the wires including connections to excitation nodes (40, 42) and detection nodes (41, 43). A nearby stationary member of the engine mounts an oscillator amplifier (55) which drives a coil (57) that excites the circuitry, and a coil (62) drives an amplifier (65) and a processor (67) which provides an indication of whether or not one or more of the wires are broken by a crack.

6 Claims, 4 Drawing Sheets

CRACK DETECTION IN FRACTURE-CRITICAL MACHINE PARTS

TECHNICAL FIELD

This invention relates to sensing the impedance of conductors disposed to span expected cracks in and near the surface of fracture-critical machinery components.

BACKGROUND ART

In gas turbine jet engines, and other rotating machinery, the designation "fracture-critical" is given to those components with enough energy, due to high rotational speeds and mass, to promote catastrophic failure. For example, in gas turbine engines, fan, compressor and turbine disks are fracture-critical. Providing containment for this type of failure is unrealistic and it is not a standard practice. Instead, fractures in the rotating components of gas turbine engines are avoided through adequate design and quality control margins, and through periodic inspections. The cost for disassembly, inspection and reassembly over the life of an engine is on the order of the initial cost of the engine.

An alternative approach to managing failures in rotating parts is use of a sensor capable of detecting impending failure with sufficient advance warning to allow timely maintenance action. A sensor that induces eddy currents in a gas turbine disk is disclosed in Barranger, J. P., "Eddy Current Jet Engine Disk-Crack Monitor", *Materials Evaluation*, Vol. 42, October 1984, pp. 1374–1378. The sensor is disposed on a stationary part adjacent the rotating part, and the combined capacitance and conductance of the device is dependent upon the integrity of the disk. Changes in electrical properties of the device are correlated with cracks in the disk.

Optical fibers have been used to monitor a condition directly, visually, and to measure the sources of structural wear, such as stress, strain and so forth, using wear indicating models to infer the actual condition. However, this technology by its very nature is hard to apply in a rotational environment such as engine disks.

The diagnostic signals of the prior art gradually degrade with time, can be analyzed only using long-term histories; can only detect cracks that actually move past the sensor; and cannot detect cracks which are remote from the sensor or hidden on the rotating part.

DISCLOSURE OF INVENTION

Objects of the invention include crack detection on machinery, including particularly rotating components: which does not require memory and long-term history; in which the diagnostic signals do not gradually degrade with time; substantially anywhere in the rotating structure; which is essentially instantaneous; in which the degree of crack progression is sensed quantumly; wherein cracks may be detected in rotating parts in which both vibratory and centrifugal forces are extremely large; wherein temperatures in the sensor and environment are extremely high; which is readily implemented using processes and materials known to have satisfactory historical usage, with low failure rates and high reliability.

According to the present invention, one or more circuits, each including one wire or several wires electrically connected in parallel with each other, are each connected between an excitation node on one end and a detection node on the other end, creating excitable closed circuits. In one embodiment, the excitation and detection nodes are inductive.

According further to the invention, the wires, excitation nodes and detection nodes are coated on the machine part by a suitable process, such as vapor deposition. The configuration of the wiring is effected by etching, utilizing techniques which are well known in the fabrication of semiconductor integrated circuits.

In further accord with the invention, materials the same as and/or compatible with the material of the machine part may be used to form the wires, excitation nodes and detection nodes.

The invention permits sensing the development of cracks in and near the surface of rotating and other parts, which cracks may be located remotely from the sensor itself, and even in hidden areas (such as on a back surface of the part). By causing the loss of one wire commensurately with each incremental length of a crack, the invention provides a quantum change in the impedance of the circuit, which is easy to process and present substantially instantaneous indications thereof.

Other objects, features and advantages of the present invention will become more apparent in the light of the following detailed description of exemplary embodiments thereof, as illustrated in the accompanying drawing.

MODE(S) FOR CARRYING OUT THE INVENTION

Figure 1:
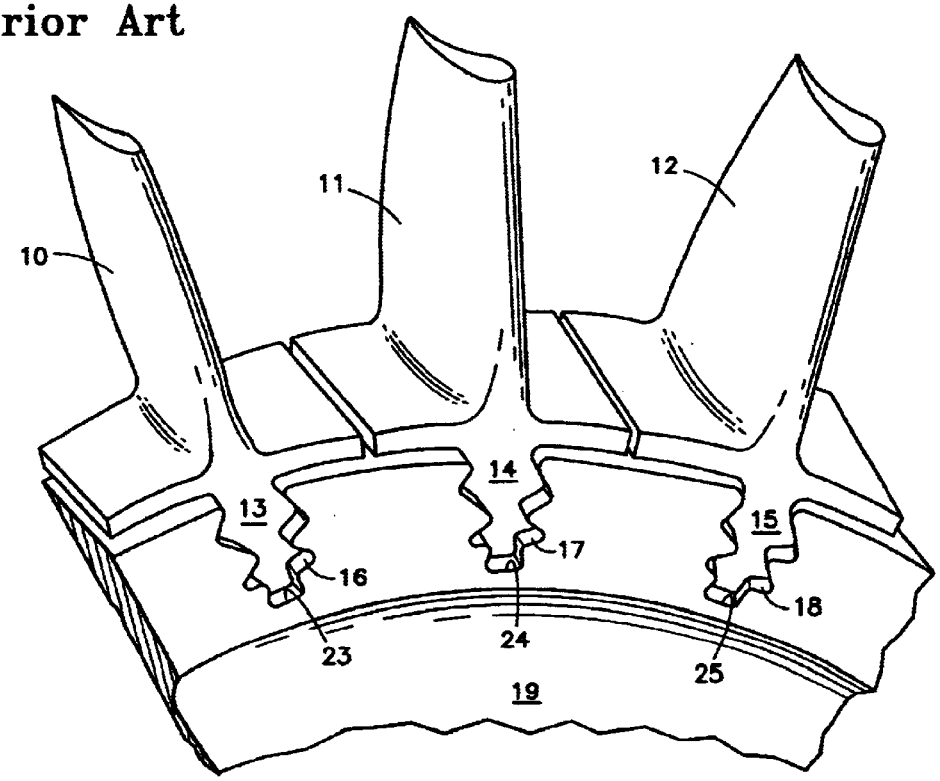
FIG. 1 is a fragmentary perspective view of a gas turbine engine turbine disk known to the art.

Referring to FIG. 1, the blades 10–12 of a gas turbine engine each have roots 13–15 which are captured by corresponding blade root sockets 16–18 in the turbine disk 19. Potential failure of an engine disk is typically preceded by cracks on and near the surface at the base 23–25 of the blade root sockets 16–18.

Figure 2:
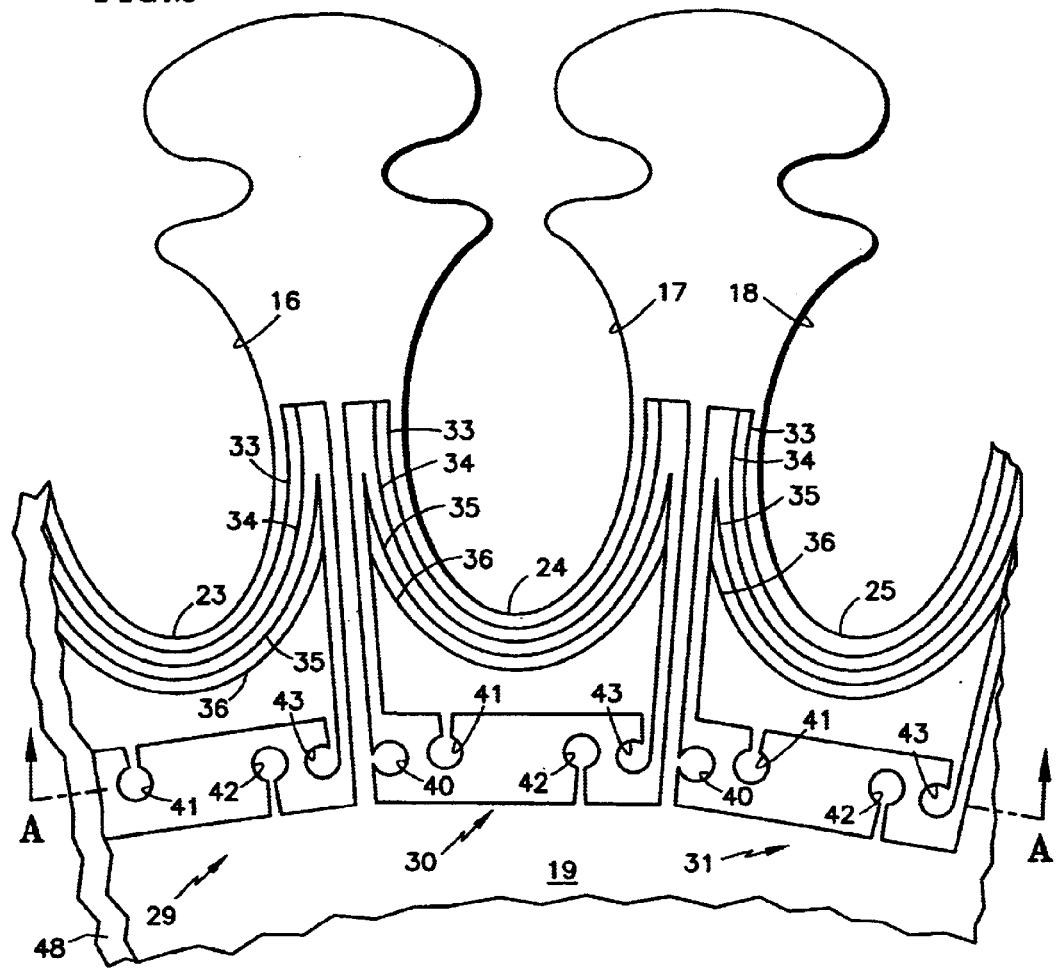
FIG. 2 is a stylized, simplified, schematic, fragmentary side elevation view of a gas turbine disk having the invention disposed thereon.
Figure 3:
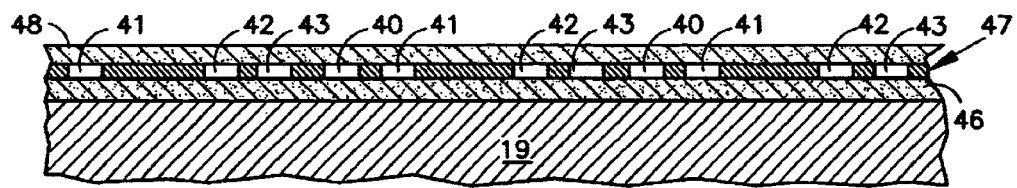
FIG. 3 is a partial, side sectional view of the disk of FIG. 2, taken on the line A—A in FIG. 2, with the vertical scale exaggerated significantly for clarity.

In FIG. 2, near the bas 23–25 of each blade root socket 16–18, a pair of circuits 29–31 each comprise a pair of wires 33, 34; 35, 36. Each pair is connected to corresponding excitation nodes 40, 41 and corresponding detection nodes 42, 43. In this embodiment, the excitation and detection nodes are inductive, and are represented in FIG. 2 as single turns of wire. In FIG. 3, assuming that the disk 19 is formed of titanium alloy, it may be first given an insulative coating 46, such as alumina on top of which there is deposited a layer 47 of titanium alloy, which after etching will form the circuitry, including the wires 33–36, the excitation and detection nodes 43, and the connections therebetween. Then, a protective coating 48 is deposited, which in this case, may also be alumina.

All of the excitation and detection nodes 40, 41; 42, 43 are disposed in a circle; that is, at the same radial distance from the axis of rotation, and in the same axial ordinate (the same plane normal to the axis of rotation). In that way, all of the excitation nodes 40, 41 will pass over the static excitation node 51 (FIG. 4) on a stationary member adjacent to the rotary part, and all of the detection nodes 42, 43 will pass adjacent to the detection node 52 on a stationary member of the engine or other apparatus. In this embodiment, the excitation and detection nodes are shown as being in the same circle; however, it may be preferable to have the excitation nodes disposed in a circle having a different radius than a circle in which the detection nodes are disposed.

Figure 5:
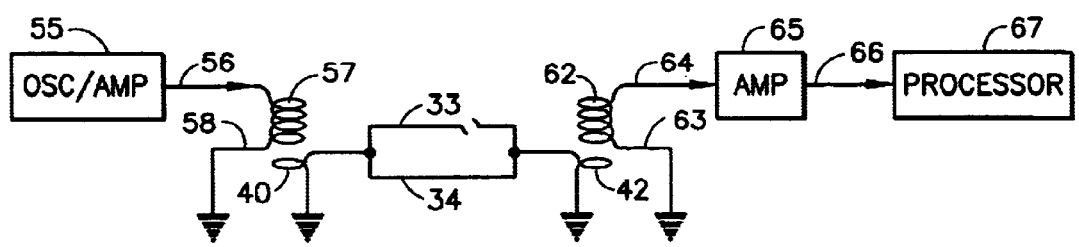
FIG. 5 is a simplified schematic diagram of the excitation and detection apparatus relative to one of the groups of wires when it is in the position to be sensed.
Figure 4:
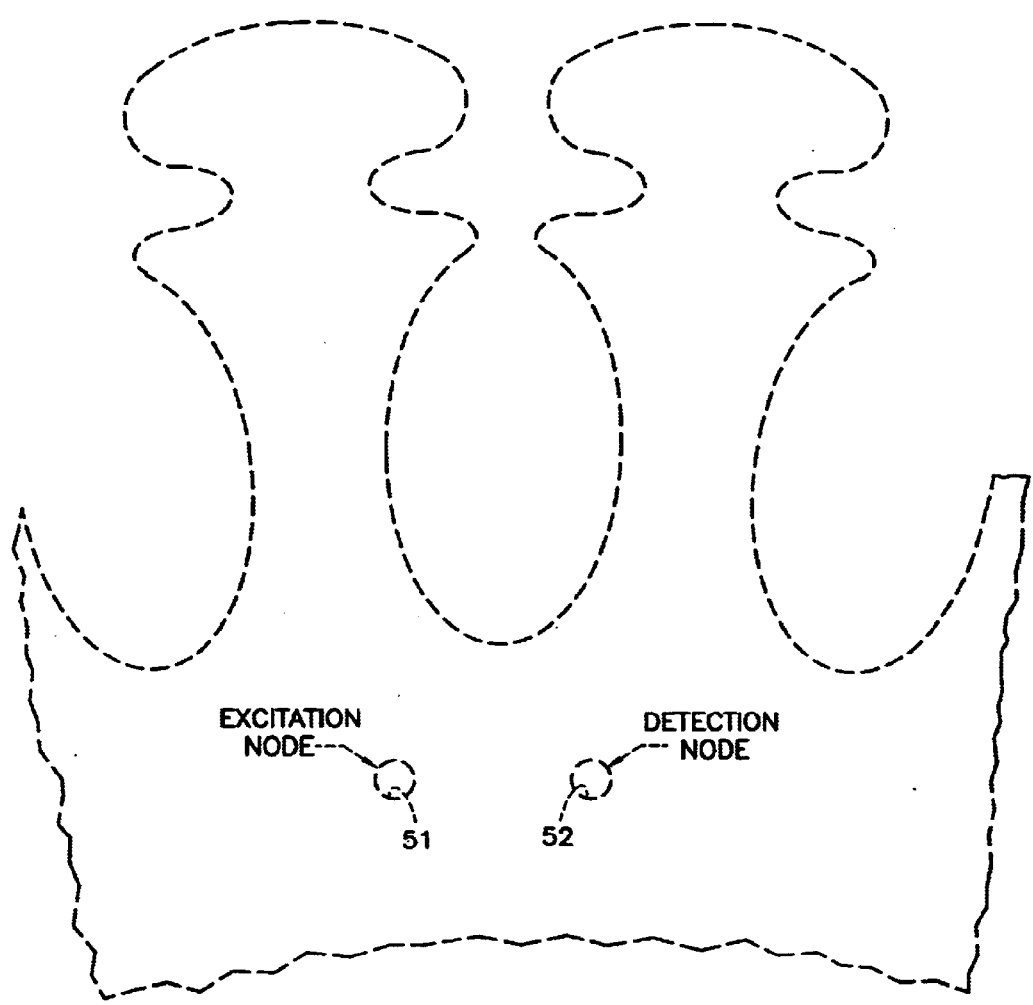
FIG. 4 is a phantom view of the fragment of disk illustrated in FIG. 2, illustrating the positions of the excitation node and the detection node relative to the blade root sockets on the disk.
Figure 6:
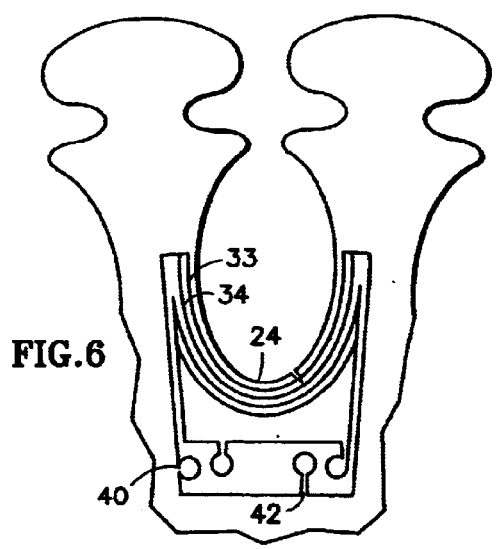
FIGS. 6–8 are stylized fragmentary side elevation views of the disk of FIG. 2 illustrating the effects of a crack as it progresses, respectively.
Figure 7:
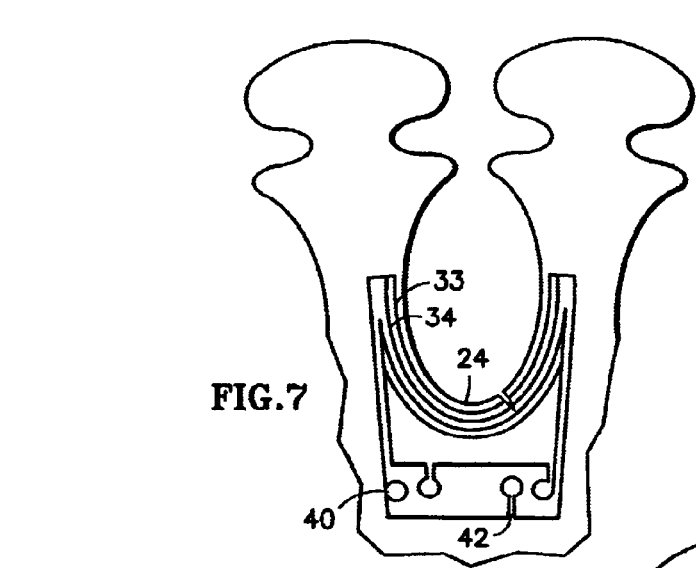
Figure 8:
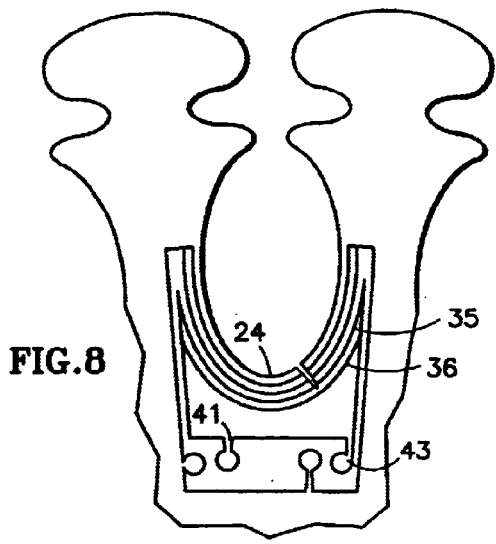

In FIG. 5, a simplified schematic illustration of the sensing apparatus of the present invention includes an oscillator/amplifier circuit 55 connected by a line 56 to a coil 57, which may be connected by a line 58 to ground. The apparatus 55–58 is disposed on a stationary member of the engine or other machinery, with the coil 57 disposed at the excitation node 51 (FIG. 4). The detection apparatus may comprise a coil 62 connected by wires 63, 64 between ground and an amplifier 65 which is connected by a line 66 to a processor 67. The oscillator/amplifier 55 may provide sinusoidal signals on the order of between 150 kHz and 200 kHz, for instance. The processor will provide an indication of whether the signal response received by the coil 62 indicates an impedance of the corresponding circuit 33, 34 or 40, 42 as being complete, a single wire being fractured, as illustrated in FIG. 5 and FIG. 6, or two wires being fractured as illustrated in FIG. 7, in which case it would be a completely open circuit. More wires may be utilized in each circuit, but the addition of each additional wire results in less of a quantum indication per wire which may be broken. If desired, the invention may be practiced with only a single wire between each pair of nodes 40–43, in which case the sensing of a crack at the position of the wire would be absolute. On the other hand, that would provide difficulty in arranging excitation and detection nodes on the disk for a suitable number of circuits. As illustrated in FIG. 8, when the crack becomes long enough to reach a second circuit, one or more of the second circuit wires 35, 36 will be broken, allowing a much more compelling alarm to be given. Of course, more circuits could be used, as well, if desired.

Likely crack locations are determined by stress analysis of the rotating part, which may be accomplished using techniques well known in the art.

The invention may be utilized while rotating the moving part at very slow speed, such as manually, or while an engine is at idle; in more sophisticated embodiments, the invention may be utilized all of the time that the rotary machinery is in operation. An aspect of the invention is that it does not rely upon the rotation of the part in order to sense the impedance of the circuit; thus it is of great value in monitoring stationary parts as well.

Thus, although the invention has been shown and described with respect to exemplary embodiments thereof, it should be understood by those skilled in the art that the foregoing and various other changes, omissions and additions may be made therein and thereto, without departing from the spirit and scope of the invention.

We claim:

1. Apparatus for sensing cracks at or near the surface of a part of a machine, comprising:
   (a) a layer of insulation disposed on said part;
   (b) a plurality of electrical conductors formed on said layer of insulation, said conductors including at least one wire electrically connected between an excitation node and a detection node, said wire being disposed across a path along which a crack may potentially form on or near the surface of said part;
   (c) exciatation means disposed on a static member of said machine for exciting said conductors through said excitation node;
   (d) detection means separate from said excitation means disposed on said static member for receiving, in response to excitation of said conductors, an electrical signal through said detection node indicative of the condition of said at least one wire and for providing a signal indicative thereof;
   (e) said excitation node provides magnetic coupling between said conductors and said excitation means;
   (f) said detection node provides electromagnetic coupling between said conductors and said detection means;
   (g) said insulation and said conductors are disposed on a rotatable part; and
   (h) a plurality of second electrical conductors formed on said layer of insulation, said second conductors including at least one wire electrically connected between a second excitation node disposed at the same radius as said first named excitation node on said rotatable part and a second detection node disposed at the same radius as said first-name detection node on said rotatable part.

2. Apparatus according to claim 1 wherein:
   said excitation node and said detection node magnetically couple said electrical circuitry to said excitation coupling means and to said detection coupling means.

3. Apparatus according to claim 1 wherein:
   said electrical conductors include at least two wires electrically connected in parallel between said nodes.

4. Apparatus according to claim 1 further comprising:
   a protective layer disposed over said electrical conductors.

5. Apparatus according to claim 1 wherein at least one wire of said second plurality of electrical conductors is disposed across the same path, along which a crack may potentially form, as said at least one wire of said first named plurality of electrical conductors.

6. Apparatus according to claim 1 wherein at least one wire of said second plurality of electrical conductors is disposed at a position on said rotary member other than across the same path, along which a crack may potentially form, as said at least one wire of said first named plurality of electrical conductors.

* * * * *